United States Patent [19]

Convers et al.

[11] 4,087,457

[45] May 2, 1978

[54] AIR INITIATION FOR DETERGENT RANGE PENDANT OR INTERNAL OLEFIN SULFITATION

[75] Inventors: Ronald J. Convers; Le Roy Rose, both of Ponca City, Okla.

[73] Assignee: Continental Oil Company, Ponca City, Okla.

[21] Appl. No.: 743,811

[22] Filed: Nov. 22, 1976

[51] Int. Cl.² ............................................. C07C 139/12
[52] U.S. Cl. .................................................. 260/513 B
[58] Field of Search ..................................... 260/513 B

[56] References Cited

U.S. PATENT DOCUMENTS

| | | | |
|---|---|---|---|
| 3,541,140 | 11/1970 | Murphy et al. | 260/513 B |
| 3,943,174 | 3/1976 | Ellis et al. | 260/513 B |
| 3,975,430 | 8/1976 | Neri et al. | 260/513 B |

OTHER PUBLICATIONS

Gilbert, "Sulfonation and Related Reactions", pp. 174-179), (1965).

*Primary Examiner*—Nicky Chan
*Attorney, Agent, or Firm*—Cortlan R. Schupbach

[57] ABSTRACT

Air initiation of pendant or internal olefin sulfitation at commercially useful rates and selectivities is achieved by stirring a mixture containing detergent range internal or pendant olefins, an alkali-metal or ammonium bisulfite, an alkali-metal or ammonium sulfite, an alkali-metal or ammonium alkane or alkylbenzene sulfonate surfactant, water, and an alcohol such as 1-propanol or 1-butanol, at ambient temperature and pressure while passing oxygen-containing gas through the mixture at a very slow rate. Bisulfite present must be in a mole ratio with respect to olefin of from 1 to 1-3 to 1 respectively, while sulfite must be present in a mole ratio to olefin of from 1 to 2-2 to 1. PH of the reaction mixture normally ranges from 5 to 6.

8 Claims, No Drawings

AIR INITIATION FOR DETERGENT RANGE PENDANT OR INTERNAL OLEFIN SULFITATION

This invention is directed toward an improved method for the air initiated sulfitation of internal and pendant olefins. More particularly, this invention relates to said improved method using a system of bisulfite and sulfite ions, solvents, and reaction conditions.

The art has long realized that alkali metal or ammonium bisulfites add to $C_{12}$ to $C_{22}$ olefins in the presence of oxidizing agents to form corresponding alkane sulfonates, commercially useful as detergents. Prior work has concentrated on the sulfitation of the most reactive olefins. These reactive olefins are alpha-olefins wherein the unsaturation is at the end of the olefinic chain. More substituted detergent range olefins ($C_{12}$ to $C_{22}$) show much slower sulfitation rates which have made their conversion to sulfonate detergents commercially unattractive, although said sulfonate products are acceptable from a use point of view. These olefins are those having unsaturation in positions pendant to the main backbone of the chain, or in positions on the backbone other than in the terminal position, designated as alpha.

In prior art processes, these olefins which are commercially unattractive have been separated from either the starting mixtures or from the reaction product after the reaction has been completed. These olefins have been of limited use and have often been a problem for disposal. It would therefore be of great benefit to provide a method whereby these olefins can be made commercially attractive for the same uses currently found for the more reactive alpha-olefins.

It is therefore an object of the present invention to provide a new and useful method for the air initiated sulfitation of pendant and internal olefins. Other objects will become apparent to those skilled in this art as the description proceeds.

It has now been discovered according to the present invention, that the air initiated sulfitation of pendant and internal olefins at rates commercially attractive, can be obtained by carrying out the reaction in the presence of (a) bisulfite to olefin mole ratios of from about 1 to 1 to about 3 to 1 respectively;
(b) sulfite to olefin mole ratios of from about 1 to 2 to about 2 to 1 respectively;
(c) bisulfite concentrations of 2 to 4 molar in water used;
(d) sulfite concentrations of 1 to 2.5 molar in water used;
(e) olefin concentrations of 0.8 to 2.5 molar in the alcohol used;
(f) An alcohol/water volume ratio of about 1 to 3 to about 3 to 1 respectively;
(g) reaction temperatures of about 0° to about 100° C;
(h) sufficient pressure to prevent reflux of the reaction mixture;
(i) sufficient agitation to produce an emulsion of said reaction mixture;
(j) under an oxygen flow rate of from about 0.1 to about 2.0 mole percent per hour based upon the moles of starting olefins.

It has long been known that air alone will initiate the sulfitation of olefins as shown in *The Journal of Organic Chemistry*, Volume 3, page 175 (1938) and the references cited therein. However, these sulfitations using air initiation have been very slow even with the relatively reactive alpha-olefins, as described in British Pat. No. 682,207, U.S. Pat. No. 3,306,931, and British Pat. No. 1,421,250. Thus it is apparent that the alpha-olefins, while much faster in reaction rates than internal olefins, remain marginal commercially, as shown in the *Journal of Applied Chemical Biotechnology*, Volume 25, pages 901–912, (1975), and U.S. Pat. No. 3,943,174. A result of this teaching has been the trend toward the use of catalysts such as nitrogen oxides at elevated temperatures and pressures, the use of involved pre-areation procedures and the use of costly peroxide or azo initiators even with the more reactive alpha-olefins. It is clear that an improved method would be of much benefit in the art.

It is therefore an object of the present invention to provide a method for increasing the reaction rates of pendant and internal detergent range olefins. Other objects will become apparent to those skilled in the art as the description proceeds.

It has now been surprisingly found that the sulfitation of even internal olefins can be carried out readily and efficiently under specific sets of conditions, without added catalysts, elevated temperature or pressure, and costly initiating agents such as peroxy or azo compounds, hypohalites, metals in high valence states, and so forth. The reaction conditions are not extreme, and although the ratios of components must be balanced within a relatively narrow range, the results are surprisingly efficient.

Concisely stated, the invention comprises efficiently stirring a detergent range internal olefin or a pendant olefin or mixtures of these olefins together with an alkali metal or ammonium bisulfite, an alkali metal or ammonium sulfite, an alkali metal or ammonium alkane or alkylbenzene sulfonate surfactant, water, and either or both of 1-propanol or 1-butanol at temperatures from 0° to about 100° C while under pressures sufficient to maintain the reaction mixture in a non-reflux state at the particular temperature chosen while passing a very slow flow of air or oxygen containing gas through or over the mixture. These conditions, while not extreme, provide the very surprising result of high rates of olefin sulfitation at reaction times of generally less than 10 hours.

Under the conditions of the present invention, the pH of the reaction mixture will vary between about 5 and 6 and will generally be in the area of about 5.5. No internal monitoring of the pH is necessary as the pH is inherent to the reaction mixture if no sulfur dioxide is lost from the reaction mixture by allowing it to reflux. Thus, the only pressure necessary in the instant process is that sufficient to keep the reaction mixture from refluxing at temperatures at or near 100° C. At lower temperatures where reflux would normally not be expected, ambient pressures are entirely sufficient for the process of the instant invention.

Representative examples of pendant and internal olefins useful in the instant invention are those in the carbon atom ranges of 12 to 22. Olefins having lower carbon atom content are not economically useful, although they are susceptible to the process of the instant invention. Olefins having carbon atom ranges greater than 22 react so slowly as to not be practical although an improvement in reaction rate will be found even with these olefins. Representative examples of useful pendant and internal olefins are $C_{12}$ to $C_{22}$ 2-alkyl-1-alkenes, $C_{12}$ to $C_{22}$ linear internal olefins or mixtures thereof. Representative examples of such olefins are:

| | |
|---|---|
| 2-butyl-1-octene | 2-ethyl-1-dodecene |
| 2-hexyl-1-decene | 2-ethyl-1-tetradecene |
| 2-butyl-1-decene | 2-octyl-1-dodecene |
| 2-hexyl-1-octene | 2-octyl-1-tetradecene |
| 2-methyl-1-pentadecene | 2-decyl-1-dodecene |
| 2-methyl-1-tridecene | | and similar olefins or their mixtures obtainable from catalytic dimerization of alpha olefins.

| | |
|---|---|
| 2-tetradecene | 5-octadecene |
| 3-tetradecene | 2-nonadecene |
| 4-tetradecene | 3-nonadecene |
| 7-tetradecene | 7-nonadecene |
| 2-pentadecene | 2-docosene |
| 3-pentadecene | 3-docosene |
| 4-pentadecene | 4-docosene |
| 2-hexadecene | 2-eicosene |
| 3-hexadecene | 3-eicosene |
| 4-hexadecene | 4-eicosene |
| 2-heptadecene | 2-heneicosene |
| 3-heptadecene | 3-heneicosene |
| 4-heptadecene | 4-heneicosene |
| 6-heptadecene | |
| 2-octadecene | |
| 3-octadecene | | and similar olefins or their mixtures obtainable by head-to-head dimerization of lower molecular weight alpha olefins, by isomerization of the corresponding alpha olefins, or by paraffin dehydrogenation.

Representative examples of compounds yielding bisulfite ions acceptable to the present invention are those which provide water soluble ions and counter-ions which are inert with respect to the present invention. Representative examples of such compounds are:
  sodium bisulfite
  ammonium bisulfite
  potassium bisulfite
  lithium bisulfite Representative examples of sulfite ion containing compounds are those which provide water soluble sulfite ions and counter-ions which are inert with respect to the instant process. Representative examples of such materials are:
  sodium sulfite
  potassium sulfite
  lithium sulfite It has also been found that the reaction can be again increased in rate if surfactant concentrations of greater than 20 mole percent with respect to beginning olefins are present in the mixture. While the reaction will take place in the absence of such surfactants, it has been found that the reaction rate increases in their presence, and it is therefore preferred to carry out the reaction in the presence of such surfactant.

Such surfactant concentrations can readily be maintained when the sulfitation is carried out as a continuous process. If the sulfitation is carried out in batches, the preferred surfactant is the deoiled, desalted product of the process described.

Oxygen flow rates into or over the liquid reaction mixture of from about 0.1 to about 2.0 mole percent per olefin per hour should be maintained. However, preferable rates are from 0.5 to 1.5 mole percent per hour. Gas mixtures containing oxygen, such as air, are preferred to pure oxygen for greater sulfitation chain initiating efficiency. In the case of the sluggishly reacting internal olefins, that is, those of higher molecular weights, higher air flow rates result in increased consumption of sulfite ion leading to decreased overall olefin conversion as well as poor selectivity toward the desired reaction. Therefore, lower air flow rates are preferred.

Normally the reaction is carried out at temperatures of from 0° to 100° C although temperatures of from about 20° to about 40° C are preferred.

The invention is more concretely described with reference to the examples below wherein all parts and percentages are by weight unless otherwise specified. The examples are intended to illustrate the present invention and should not be construed to limit it.

Example 1 is a comparative example showing olefin conversion in the absence of alcohol, surfactant, and sulfite. Example 2 shows the addition of alcohol, while Example 3 shows the addition of surfactant and sulfite to the process of Example 2. Example 4 doubles the sulfite content of Example 3, and Example 5 further increases the sulfite concentration. Examples 6–10 show the effect of temperature at various air flows. Examples 11 and 12 show the effect of various air flows at uniform temperatures.

EXAMPLE 1

A mixture of 8.40 grams of mixed $C_{12}$ linear internal olefins obtained by the $Fe(CO)_5$ isomerization of 1-dodecene, 0.84 grams of n-tetradecane as a gas liquid chromatograph (GLC) standard, 20.1 grams of $NaHSO_3$ and 80 ml of water were stirred at about 200 (rpm) revolutions per minute under a nitrogen atmosphere. Reaction was initiated at ambient temperature and pressure by a 3.7 ml per minute air flow over the solution and was monitored periodically by GLC. No olefin conversion was observed after 6 hours.

EXAMPLE 2

A mixture as described in Example 1 with the exception of an additional 40 ml of 1-propanol was stirred at about 2,000 rpm under a nitrogen atmosphere. The reaction was initiated at ambient temperature and pressure by a 3.7 ml per minute air flow into the liquid by a sintered glass sparger and monitored by GLC as described above. Olefin conversion after 6 hours was 32%.

EXAMPLE 3

A mixture of mixed $C_{12}$ linear internal olefins as previously described was mixed with 0.84 grams of n-tetradecane, 15.3 grams of $NaHSO_3$, 1.3 grams of $Na_2SO_3$, 20 grams of 51.6% sodium alkylbenzenesulfonates having a molecular weight of 340 in an alcohol/water solvent system comprising 40 ml of water and 40 ml of 1-propanol was stirred at about 2,000 rpm's under nitrogen. Reaction was initiated at ambient temperature and pressure with a 1.0 ml per minute air flow into the liquid via a sintered glass sparger, and was monitored periodically by GLC. Olefin conversions after 6 and 7 hours respectively were 48 and 48%.

EXAMPLE 4

A mixture was prepared exactly as described in Example 3 except that 2.5 grams of $Na_2SO_3$ was used. Reaction was initiated at ambient temperature and pressure with a 3.7 ml per minute air flow into the liquid via a sintered glass sparger. Olefin conversions after 6 and 7 hours were 57 and 58% respectively.

EXAMPLE 5

A mixture was prepared exactly as described in Example 3 except that 4 grams of $Na_2SO_3$ was used at 7.5 ml per minute air flow. Olefin conversions after 6 and 7 hours were 66 and 68% respectively.

EXAMPLE 6

Example 5 was repeated but with initiation by a 1.0 ml per minute air flow. Olefin conversions after 6 and 7 hours were 67 and 70% respectively.

EXAMPLE 7

Example 5 was repeated but at 50° C. Olefin conversions after 6 and 7 hours were both 55%.

EXAMPLE 8

Example 6 was repeated but at 50° C. Olefin conversion after 6 and 7 hours were both 60%.

EXAMPLE 9

Example 5 was repeated but at 0° to 5° C. Olefin conversions after 6 and 7 hours were 47 and 48% respectively.

EXAMPLE 10

Example 6 was repeated but at 0° to 5° C. Olefin conversions after 6 and 7 hours were 60 and 63% respectively.

EXAMPLE 11

A mixture of 8.4 grams of linear internal olefins as previously described, 0.84 grams of n-tetradecane, 13.3 grams of $NaHSO_3$, 8 grams of $Na_2SO_3$, 20 grams of 51.6% sodium alkylbenzenesulfonates in 40 ml of water, and 40 ml of 1-propanol was stirred at about 2,000 rmp under nitrogen. Reaction was initiated at ambient temperature and pressure by a 2.8 ml per minute air flow into the liquid via a sintered glass sparger and was monitored periodically by GLC. Olefin conversions after 6 and 7 hours were 68 and 72% respectively.

EXAMPLE 12

Example 11 was repeated but with initiation by a 0.5 ml per minute air flow. Olefin conversions after 6 and 7 hours were 79 and 83% respectively.

It can be seen from the above examples that a great improvement has been made in the air initiated sulfitation of internal and pendant olefins. It has surprisingly been discovered that air flow must be decreased when dealing with higher molecular weight olefins in order to carry the reaction to higher levels of conversion. It is readily apparent that a significant advance has been made in the art.

While certain embodiments and details have been shown for the purpose of illustrating this invention, it will be apparent to those skilled in this art that various changes and modifications may be made herein without departing from the spirit or the scope of the invention.

We claim:

1. A method for the air initiated sulfitation of pendant and internal olefins containing from 12 to 22 carbon atoms comprising carrying out the reaction in the presence of:

(a) bisulfite to olefin mole ratios of from 1:1 to 3:1 in an alcohol/water system, wherein said alcohol is 1-propanol, 1-butanol, or both 1-propanol and 1-butanol, and said bisulfite is obtained from compounds yielding water-soluble bisulfite ions and counter-ions which are inert with respect to the reaction and selected from the group consisting of sodium bisulfite, ammonium bisulfite, potassium bisulfite, and lithium bisulfite;
    (b) sulfite to olefin mole ratios of from 1:1 to 2:1 in said alcohol/water system, said sulfite being obtained from compounds which provide water soluble sulfite ions and counter-ions which are inert with respect to the reaction and selected from the group consisting of sodium sulfite, potassium sulfite and lithium sulfite;
    (c) bisulfite concentrations of about 2 to about 4 molar in the water used;
    (d) sulfite concentrations of from about 1 to about 2.5 molar in the water used;
    (e) olefin concentrations of .8 to 2.5 molar in the alcohol used;
    (f) an alcohol/water volume ratio of 1:3 to 3:1;
    (g) reaction temperatures of 0° to about 100° C;
    (h) sufficient pressure to prevent reflux of the reaction mixture;
    (i) sufficient agitation to produce an emulsion of said reaction mixture;
    (j) under an oxygen flow rate of about 0.1 to about 2.0 moles percent per hour based upon the starting olefins.

2. A method as described in claim 1 wherein in addition a surfactant is present in a concentration of greater than 20 mole percent with respect to the olefin.

3. A method as described in claim 2 wherein the surfactant is the deoiled, desalted product of the process.

4. A method as described in claim 2 wherein the concentration of (d) is from about 1 to about 1.5 molar in water, and (f) has a volume ratio of water to alcohol of from about 1 to 1 to about 2 to 1 respectively.

5. A method as described in claim 4 wherein the temperature is from about 20° to about 40° C.

6. A method as described in claim 5 wherein the oxygen flow rate is from about 0.5 to about 1.5 mole percent per hour based upon the olefins present.

7. A method as described in claim 6 wherein the olefin is selected from the group consisting of $C_{12}$ to $C_{22}$ 2-alkyl-1-alkenes, $C_{12}$ to $C_{22}$ linear internal olefins, or mixtures thereof.

8. A method as described in claim 7 wherein the olefin is selected from the group consisting of

| | |
|---|---|
| 2-tetradecene | 5-octadecene |
| 3-tetradecene | 2-nonadecene |
| 4-tetradecene | 3-nonadecene |
| 7-tetradecene | 7-nonadecene |
| 2-pentadecene | 2-docosene |
| 3-pentadecene | 3-docosene |
| 4-pentadecene | 4-docosene |
| 2-hexadecene | 2-eicosene |
| 3-hexadecene | 3-eicosene |
| 2-heptadecene | 2-heneicosene |
| 3-heptadecene | 3-heneicosene |
| 4-heptadecene | 4-heneicosene |
| 6-heptadecene | |
| 2-octadecene | |
| 3-octadecene | |

* * * * *